United States Patent
Stern et al.

(10) Patent No.: US 7,141,049 B2
(45) Date of Patent: Nov. 28, 2006

(54) HANDPIECE FOR TREATMENT OF TISSUE

(75) Inventors: Roger Stern, Cupertino, CA (US); Mitchell Levinson, Pleasanton, CA (US); Bryan Weber, Livermore, CA (US)

(73) Assignee: Thermage, Inc., Hayward, CA (US)

( * ) Notice: Subject to any disclaimer, the term of this patent is extended or adjusted under 35 U.S.C. 154(b) by 469 days.

(21) Appl. No.: 10/072,610

(22) Filed: Feb. 6, 2002

(65) Prior Publication Data
US 2004/0111087 A1 Jun. 10, 2004

Related U.S. Application Data

(63) Continuation-in-part of application No. 09/522,275, filed on Mar. 9, 2000, now Pat. No. 6,413,255.

(60) Provisional application No. 60/123,440, filed on Mar. 9, 1999.

(51) Int. Cl.
A61B 18/18 (2006.01)

(52) U.S. Cl. .......................... 606/41; 606/99

(58) Field of Classification Search ............ 606/27–52, 606/41, 42, 48, 39, 50; 607/97–99, 101
See application file for complete search history.

(56) References Cited

U.S. PATENT DOCUMENTS

| | | | |
|---|---|---|---|
| 3,831,604 A | 8/1974 | Neefe ........................ 128/260 |
| 4,074,718 A | 2/1978 | Morrison, Jr. ......... 128/303.14 |
| 4,140,130 A | 2/1979 | Storm, III ................... 128/404 |
| 4,164,226 A | 8/1979 | Tapper ................... 128/419 R |
| 4,290,435 A | 9/1981 | Waggott ..................... 128/800 |
| 4,343,301 A | 8/1982 | Indech ........................ 128/24 |
| 4,346,715 A | 8/1982 | Gammell .................... 128/422 |
| 4,375,220 A | 3/1983 | Matvias ...................... 128/804 |
| 4,381,007 A | 4/1983 | Doss ........................ 128/303.1 |
| 4,441,486 A | 4/1984 | Pounds ........................ 128/24 |
| 4,545,368 A | 10/1985 | Rand et al. .................. 128/1.3 |
| 4,556,070 A | 12/1985 | Vaguine et al. |
| 4,585,237 A | 4/1986 | Koop |
| 4,633,875 A | 1/1987 | Turner |
| 4,646,737 A | 3/1987 | Hussein et al. |
| 4,655,215 A * | 4/1987 | Pike ............................ 606/42 |
| 4,676,258 A | 6/1987 | Inokuchi et al. ............ 128/804 |
| 4,709,372 A | 11/1987 | Rando et al. |
| 4,709,701 A | 12/1987 | Weber ........................ 128/422 |
| 4,754,754 A | 7/1988 | Garito et al. .......... 128/303.14 |
| 4,756,310 A | 7/1988 | Bitterly ...................... 128/400 |
| RE32,849 E | 1/1989 | Wei et al. .............. 204/192.27 |

(Continued)

FOREIGN PATENT DOCUMENTS

DE 1 949 534 4/1970

(Continued)

OTHER PUBLICATIONS

Anvari, et al., "Dynamic Epidermal Cooling in Conjunction with Laser Treatment of Port-Wine Stains: Theoretical and Preliminary Clinical Evaluations", *Lasers in Medical Science* 10: 105-112, (Jul. 1995).

(Continued)

*Primary Examiner*—Roy D. Gibson
*Assistant Examiner*—Pete Vrettakos
(74) *Attorney, Agent, or Firm*—Wood, Herron & Evans, L.L.P.

(57) ABSTRACT

A handpiece that includes a handpiece assembly, a handpiece housing and a cooling fluidic medium valve member. An electrode assembly is coupled to the handpiece housing. The electrode assembly has a least one RF electrode that is capacitively coupled to a skin surface when at least a portion of the RF electrode is in contact with the skin surface.

56 Claims, 4 Drawing Sheets

U.S. PATENT DOCUMENTS

| | | | |
|---|---|---|---|
| 4,864,098 A | 9/1989 | Basanese et al. | |
| 4,881,543 A | 11/1989 | Trembly et al. | 128/303.1 |
| 4,887,614 A | 12/1989 | Shirakami et al. | 128/798 |
| 4,889,122 A | 12/1989 | Watmough et al. | 128/399 |
| 4,891,820 A | 1/1990 | Rando et al. | |
| 4,944,302 A | 7/1990 | Hernandez et al. | 128/798 |
| 4,957,480 A | 9/1990 | Morenings | 604/20 |
| 4,962,761 A | 10/1990 | Golden | 128/400 |
| 4,976,709 A | 12/1990 | Sand | 606/5 |
| 5,003,991 A | 4/1991 | Takayama et al. | 128/784 |
| 5,011,483 A | 4/1991 | Sleister | |
| 5,041,110 A * | 8/1991 | Fleenor | 606/34 |
| 5,057,104 A | 10/1991 | Chess | |
| 5,100,402 A | 3/1992 | Fan | 606/37 |
| 5,107,832 A | 4/1992 | Guibert et al. | |
| 5,131,904 A | 7/1992 | Markoll | |
| 5,133,351 A | 7/1992 | Masaki | 128/419 R |
| 5,136,676 A | 8/1992 | Arnett et al. | |
| 5,143,063 A | 9/1992 | Fellner | 128/399 |
| 5,186,181 A | 2/1993 | Franconi et al. | 128/804 |
| 5,190,031 A | 3/1993 | Guibert et al. | |
| 5,190,517 A | 3/1993 | Zieve et al. | 604/22 |
| 5,217,455 A | 6/1993 | Tan | 606/9 |
| 5,230,334 A | 7/1993 | Klopotek | 128/399 |
| 5,231,997 A | 8/1993 | Kikuchi et al. | |
| 5,234,428 A * | 8/1993 | Kaufman | 606/45 |
| 5,249,192 A | 9/1993 | Kuizenga et al. | 372/23 |
| 5,249,575 A | 10/1993 | DiMino et al. | 607/150 |
| 5,282,797 A | 2/1994 | Chess | 606/9 |
| 5,290,273 A | 3/1994 | Tan | 606/3 |
| 5,300,097 A | 4/1994 | Lerner et al. | 607/93 |
| 5,304,169 A | 4/1994 | Sand | 606/5 |
| 5,304,171 A | 4/1994 | Gregory et al. | 606/15 |
| 5,312,395 A | 5/1994 | Tan et al. | |
| 5,315,994 A | 5/1994 | Guibert et al. | 607/101 |
| 5,334,193 A | 8/1994 | Nardella | 606/41 |
| 5,342,357 A | 8/1994 | Nardella | 606/40 |
| 5,344,418 A | 9/1994 | Ghaffari | |
| 5,348,554 A | 9/1994 | Imran et al. | 606/41 |
| 5,360,447 A | 11/1994 | Koop | 623/15 |
| 5,364,394 A | 11/1994 | Mehl | |
| 5,366,443 A | 11/1994 | Eggers et al. | |
| 5,370,642 A | 12/1994 | Keller | 606/9 |
| 5,374,265 A | 12/1994 | Sand | 606/5 |
| 5,387,176 A | 2/1995 | Markoll | |
| 5,395,363 A * | 3/1995 | Billings et al. | 606/41 |
| 5,396,887 A * | 3/1995 | Imran | 600/374 |
| 5,397,327 A | 3/1995 | Koop et al. | |
| 5,401,272 A | 3/1995 | Perkins | |
| 5,405,368 A | 4/1995 | Eckhouse | |
| 5,423,807 A | 6/1995 | Milder | 606/20 |
| 5,423,811 A | 6/1995 | Imran et al. | 606/41 |
| 5,437,662 A | 8/1995 | Nardella | 606/40 |
| 5,454,808 A | 10/1995 | Koop et al. | |
| 5,456,260 A | 10/1995 | Kollias et al. | 128/665 |
| 5,458,596 A | 10/1995 | Lax et al. | 606/31 |
| 5,462,521 A | 10/1995 | Brucker et al. | 604/20 |
| 5,464,436 A | 11/1995 | Smith | 607/89 |
| 5,486,172 A | 1/1996 | Chess | |
| 5,496,312 A | 3/1996 | Klicek | |
| 5,496,314 A | 3/1996 | Eggers | 606/41 |
| 5,500,012 A | 3/1996 | Brucker et al. | 607/122 |
| 5,507,790 A | 4/1996 | Weiss | |
| 5,509,916 A | 4/1996 | Taylor | |
| 5,522,813 A | 6/1996 | Trelles | 606/2 |
| 5,522,814 A | 6/1996 | Bernaz | |
| 5,527,308 A | 6/1996 | Anderson et al. | 606/14 |
| 5,527,350 A | 6/1996 | Grove et al. | 607/89 |
| 5,531,739 A | 7/1996 | Trelles | 606/2.5 |
| 5,556,377 A | 9/1996 | Rosen et al. | 604/22 |
| 5,556,612 A | 9/1996 | Anderson et al. | 424/59 |
| 5,558,667 A | 9/1996 | Yarborough et al. | 606/9 |
| 5,569,242 A | 10/1996 | Lax et al. | 606/42 |
| 5,571,216 A | 11/1996 | Anderson | 623/66 |
| 5,578,029 A | 11/1996 | Trelles et al. | 606/25 |
| 5,595,568 A | 1/1997 | Anderson et al. | 606/9 |
| 5,599,342 A | 2/1997 | Hsia et al. | 606/9 |
| 5,609,573 A | 3/1997 | Sandock | 604/22 |
| 5,620,478 A | 4/1997 | Eckhouse | |
| 5,626,631 A | 5/1997 | Eckhouse | |
| 5,628,744 A | 5/1997 | Coleman et al. | |
| 5,630,426 A | 5/1997 | Eggers et al. | 128/734 |
| 5,643,334 A | 7/1997 | Eckhouse et al. | 607/88 |
| 5,649,923 A | 7/1997 | Gregory et al. | 606/15 |
| 5,655,547 A | 8/1997 | Karni | 128/898 |
| 5,660,836 A | 8/1997 | Knowlton | 424/400 |
| 5,669,868 A | 9/1997 | Markoll | |
| 5,681,282 A | 10/1997 | Eggers et al. | |
| 5,683,366 A | 11/1997 | Eggers et al. | |
| 5,683,380 A | 11/1997 | Eckhouse et al. | |
| 5,692,058 A | 11/1997 | Eggers et al. | |
| 5,693,045 A | 12/1997 | Eggers | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,707,402 A * | 1/1998 | Heim | 607/88 |
| 5,720,772 A | 2/1998 | Eckhouse | |
| 5,730,719 A | 3/1998 | Edwards | |
| 5,735,844 A | 4/1998 | Anderson et al. | 606/9 |
| 5,743,901 A | 4/1998 | Grove et al. | 606/9 |
| 5,746,735 A | 5/1998 | Furumoto et al. | 606/9 |
| 5,749,868 A | 5/1998 | Furumoto | 606/9 |
| 5,754,573 A | 5/1998 | Yarborough et al. | 372/22 |
| 5,755,751 A | 5/1998 | Eckhouse | |
| 5,755,753 A * | 5/1998 | Knowlton | 607/98 |
| 5,769,879 A | 6/1998 | Richards et al. | 607/101 |
| 5,775,338 A | 7/1998 | Hastings | 128/898 |
| 5,776,092 A | 7/1998 | Farin et al. | 604/22 |
| 5,776,175 A | 7/1998 | Eckhouse et al. | 607/100 |
| 5,810,801 A | 9/1998 | Anderson et al. | 606/9 |
| 5,814,008 A | 9/1998 | Chen et al. | 604/21 |
| 5,814,040 A | 9/1998 | Nelson et al. | 606/9 |
| 5,814,041 A | 9/1998 | Anderson et al. | 606/15 |
| 5,820,626 A | 10/1998 | Baumgardner | 606/13 |
| 5,833,612 A | 11/1998 | Eckhouse et al. | 600/476 |
| 5,836,999 A | 11/1998 | Eckhouse et al. | 607/88 |
| 5,843,072 A | 12/1998 | Furumoto et al. | 606/9 |
| 5,843,078 A | 12/1998 | Sharkey | 606/41 |
| 5,849,029 A | 12/1998 | Eckhouse et al. | |
| 5,851,181 A | 12/1998 | Talmor | |
| 5,871,479 A | 2/1999 | Furumoto et al. | 606/9 |
| 5,879,326 A | 3/1999 | Godshall et al. | 604/51 |
| 5,879,346 A | 3/1999 | Waldman et al. | |
| 5,880,880 A | 3/1999 | Anderson et al. | 359/385 |
| 5,885,273 A | 3/1999 | Eckhouse et al. | |
| 5,885,274 A | 3/1999 | Fullmer et al. | 606/9 |
| 5,906,609 A | 5/1999 | Assa et al. | 606/9 |
| 5,911,718 A | 6/1999 | Yarborough et al. | 606/9 |
| 5,919,219 A | 7/1999 | Knowlton | 607/102 |
| 5,925,078 A | 7/1999 | Anderson | 623/66 |
| 5,938,657 A | 8/1999 | Assa et al. | 606/9 |
| 5,948,009 A | 9/1999 | Tu | 607/96 |
| 5,948,011 A | 9/1999 | Knowlton | 607/101 |
| 5,964,749 A | 10/1999 | Eckhouse et al. | 606/9 |
| 5,968,034 A | 10/1999 | Fullmer et al. | 606/9 |
| 5,970,983 A | 10/1999 | Karni et al. | 128/898 |
| 5,979,454 A | 11/1999 | Anvari et al. | 128/898 |
| 5,983,900 A | 11/1999 | Clement et al. | 128/898 |
| 5,995,283 A | 11/1999 | Anderson et al. | 359/385 |
| 5,997,530 A | 12/1999 | Nelson et al. | |
| 6,014,579 A | 1/2000 | Pomeranz et al. | 600/374 |
| 6,015,404 A | 1/2000 | Altshuler et al. | |
| 6,027,495 A | 2/2000 | Miller | |

| Patent | Date | Inventor | Class |
|---|---|---|---|
| RE36,634 E | 3/2000 | Ghaffari | |
| 6,045,548 A | 4/2000 | Furumoto et al. | 606/9 |
| 6,047,215 A | 4/2000 | McClure et al. | 607/101 |
| 6,050,990 A | 4/2000 | Tankovich et al. | |
| 6,053,909 A | 4/2000 | Shadduck | |
| 6,066,130 A | 5/2000 | Gregory et al. | 606/15 |
| 6,077,294 A | 6/2000 | Cho et al. | 607/89 |
| 6,081,749 A | 6/2000 | Ingle et al. | 607/101 |
| 6,090,101 A | 7/2000 | Quon et al. | 606/9 |
| 6,104,959 A | 8/2000 | Spertell | 607/101 |
| 6,120,497 A | 9/2000 | Anderson et al. | 606/9 |
| 6,126,655 A | 10/2000 | Domankivitz et al. | 606/17 |
| 6,129,723 A | 10/2000 | Anderson et al. | 606/13 |
| 6,139,569 A | 10/2000 | Ingle et al. | 607/104 |
| 6,139,653 A | 10/2000 | Fernandes et al. | 148/439 |
| 6,147,503 A | 11/2000 | Nelson et al. | |
| 6,159,194 A | 12/2000 | Eggers et al. | |
| 6,162,212 A | 12/2000 | Kreindel et al. | 606/9 |
| 6,168,590 B1 | 1/2001 | Neev | 606/9 |
| 6,169,926 B1 | 1/2001 | Baker | 607/99 |
| 6,171,301 B1 | 1/2001 | Nelson et al. | 606/9 |
| 6,183,773 B1 | 2/2001 | Anderson | |
| 6,187,001 B1 | 2/2001 | Azar et al. | |
| 6,200,308 B1 | 3/2001 | Pope et al. | |
| 6,210,402 B1 | 4/2001 | Olsen et al. | 606/32 |
| 6,214,034 B1 | 4/2001 | Azar | |
| 6,228,075 B1 | 5/2001 | Furumoto | 606/9 |
| 6,228,078 B1 | 5/2001 | Eggers et al. | 606/32 |
| 6,235,024 B1 | 5/2001 | Tu | 606/41 |
| 6,240,925 B1 | 6/2001 | McMillan et al. | 128/898 |
| 6,241,753 B1 | 6/2001 | Knowlton | 607/99 |
| 6,248,103 B1 | 6/2001 | Tannenbaum et al. | 606/9 |
| 6,254,594 B1 | 7/2001 | Berry | |
| 6,267,758 B1 | 7/2001 | Daw et al. | |
| 6,273,883 B1 | 8/2001 | Furumoto | 606/9 |
| 6,273,884 B1 | 8/2001 | Altshuler et al. | 606/9 |
| 6,273,885 B1 | 8/2001 | Koop et al. | 606/9 |
| 6,275,962 B1 | 8/2001 | Fuller et al. | 714/724 |
| 6,277,116 B1 | 8/2001 | Utely et al. | 606/42 |
| 6,280,438 B1 | 8/2001 | Eckhouse et al. | |
| 6,283,956 B1 | 9/2001 | McDaniel | |
| 6,299,620 B1 | 10/2001 | Shadduck et al. | |
| 6,311,090 B1 | 10/2001 | Knowlton | 607/101 |
| 6,334,074 B1 | 12/2001 | Spertell | 607/101 |
| 6,336,926 B1 | 1/2002 | Goble | 606/34 |
| 6,337,998 B1 | 1/2002 | Behl et al. | 607/101 |
| 6,350,261 B1 | 2/2002 | Domankivitz et al. | 606/17 |
| 6,350,276 B1 | 2/2002 | Knowlton | 607/104 |
| 6,377,854 B1 | 4/2002 | Knowlton | 607/101 |
| 6,377,855 B1 | 4/2002 | Knowlton | 607/101 |
| 6,381,497 B1 | 4/2002 | Knowlton | 607/101 |
| 6,381,498 B1 | 4/2002 | Knowlton | 607/101 |
| 6,383,176 B1 | 5/2002 | Connors et al. | 606/9 |
| 6,387,089 B1 | 5/2002 | Kreindel et al. | 606/9 |
| 6,387,103 B1 | 5/2002 | Shadduck | |
| 6,387,380 B1 | 5/2002 | Knowlton | 424/400 |
| 6,402,739 B1 | 6/2002 | Neev | |
| 6,405,090 B1 | 6/2002 | Knowlton | 607/102 |
| 6,408,212 B1 | 6/2002 | Neev | |
| 6,413,253 B1 | 7/2002 | Koop et al. | |
| 6,413,255 B1 | 7/2002 | Stern | 606/41 |
| 6,425,912 B1 | 7/2002 | Knowlton | 607/101 |
| 6,430,446 B1 | 8/2002 | Knowlton | 607/101 |
| 6,436,094 B1 | 8/2002 | Reuter | 606/9 |
| 6,451,007 B1 | 9/2002 | Koop et al. | |
| 6,453,202 B1 | 9/2002 | Knowlton | 607/102 |
| 6,463,336 B1 | 10/2002 | Mawhinney | |
| 6,485,484 B1 | 11/2002 | Connors et al. | |
| 6,488,696 B1 | 12/2002 | Cho et al. | |
| 6,500,141 B1 | 12/2002 | Irion et al. | 604/32 |
| 6,508,813 B1 | 1/2003 | Altshuler | |
| 6,511,475 B1 | 1/2003 | Altshuler et al. | 606/9 |
| 6,514,243 B1 | 2/2003 | Eckhouse et al. | |
| 6,514,244 B1 | 2/2003 | Pope et al. | |
| 6,527,763 B1 | 3/2003 | Esch et al. | 606/2 |
| 6,529,543 B1 | 3/2003 | Anderson et al. | 372/108 |
| 6,533,775 B1 | 3/2003 | Rizoiu | |
| 6,569,155 B1 | 5/2003 | Connors et al. | |
| 6,600,951 B1 | 7/2003 | Anderson | |
| 6,605,079 B1 | 8/2003 | Shanks et al. | |
| 6,605,080 B1 | 8/2003 | Altshuler et al. | 606/3 |
| 6,623,454 B1 | 9/2003 | Eggers et al. | |
| 6,629,974 B1 | 10/2003 | Penny et al. | |
| 6,632,218 B1 | 10/2003 | Furumoto et al. | |
| 6,649,904 B1 | 11/2003 | Hayashi et al. | |
| 6,653,618 B1 | 11/2003 | Zenzie | |
| 6,659,999 B1 | 12/2003 | Anderson et al. | 606/9 |
| 6,662,054 B1 | 12/2003 | Kreindel et al. | |
| 6,666,856 B1 | 12/2003 | Connors et al. | |
| 6,702,808 B1 | 3/2004 | Kreindel | |
| 6,702,838 B1 | 3/2004 | Anderson et al. | |
| 6,706,032 B1 | 3/2004 | Weaver et al. | 604/500 |
| 6,723,090 B1 | 4/2004 | Altshuler et al. | |
| 6,743,222 B1 | 6/2004 | Durkin et al. | |
| 6,749,602 B1 | 6/2004 | Sierra et al. | |
| 6,749,624 B1 | 6/2004 | Knowlton | 607/104 |
| 6,758,845 B1 | 7/2004 | Weckwerth et al. | |
| 2001/0037118 A1 | 11/2001 | Shadduck | |
| 2001/0049524 A1 | 12/2001 | Morgan et al. | 606/50 |
| 2002/0016587 A1 | 2/2002 | Furumoto | 606/7 |
| 2002/0016601 A1 | 2/2002 | Shadduck | |
| 2002/0019625 A1 | 2/2002 | Azar | |
| 2002/0022827 A1 | 2/2002 | Esch et al. | 606/7 |
| 2002/0035360 A1 | 3/2002 | Conners et al. | 606/9 |
| 2002/0049433 A1 | 4/2002 | Furumoto et al. | 606/9 |
| 2002/0065533 A1 | 5/2002 | Weaver et al. | 606/191 |
| 2002/0091377 A1 | 7/2002 | Anderson et al. | 606/9 |
| 2002/0111605 A1 | 8/2002 | Furumoto et al. | 606/3 |
| 2002/0123743 A1 | 9/2002 | Shanks et al. | |
| 2002/0123745 A1 | 9/2002 | Svaasand et al. | 606/9 |
| 2002/0151887 A1 | 10/2002 | Stern et al. | 606/41 |
| 2002/0156471 A1 | 10/2002 | Stern et al. | 606/41 |
| 2002/0161357 A1 | 10/2002 | Anderson et al. | 606/9 |
| 2002/0161362 A1 | 10/2002 | Penny et al. | |
| 2002/0183724 A1 | 12/2002 | Neev | |
| 2002/0183789 A1 | 12/2002 | Neev | |
| 2003/0023283 A1 | 1/2003 | McDaniel | |
| 2003/0028186 A1 | 2/2003 | Kreindel | |
| 2003/0032950 A1 | 2/2003 | Altshuler et al. | |
| 2003/0036751 A1 | 2/2003 | Anderson et al. | 606/9 |
| 2003/0040739 A1 | 2/2003 | Koop | |
| 2003/0055414 A1 | 3/2003 | Altshuler et al. | 606/9 |
| 2003/0059386 A1 | 3/2003 | Sumian et al. | |
| 2003/0065313 A1 | 4/2003 | Koop et al. | |
| 2003/0065314 A1 | 4/2003 | Altshuler et al. | |
| 2003/0069567 A1 | 4/2003 | Eckhouse et al. | |
| 2003/0097162 A1 | 5/2003 | Kreindel | |
| 2003/0129154 A1 | 7/2003 | McDaniel | |
| 2003/0130710 A1 | 7/2003 | Baker et al. | |
| 2003/0139740 A1 | 7/2003 | Kreindel | |
| 2003/0163178 A1 | 8/2003 | Davison et al. | |
| 2003/0187488 A1 | 10/2003 | Kreindel et al. | |
| 2003/0199859 A1 | 10/2003 | Altshuler et al. | 606/9 |
| 2003/0199866 A1 | 10/2003 | Stern et al. | |
| 2003/0208326 A1 | 11/2003 | Chen et al. | 702/49 |
| 2003/0212393 A1 | 11/2003 | Knowlton et al. | |
| 2003/0216728 A1 | 11/2003 | Stern et al. | |
| 2003/0218756 A1 | 11/2003 | Chen et al. | 356/497 |
| 2003/0220749 A1 | 11/2003 | Chen et al. | 702/31 |
| 2003/0233138 A1 | 12/2003 | Spooner | |
| 2003/0236487 A1 | 12/2003 | Knowlton | |
| 2004/0000316 A1 | 1/2004 | Knowlton et al. | |
| 2004/0002704 A1 | 1/2004 | Knowlton et al. | |
| 2004/0002705 A1 | 1/2004 | Knowlton et al. | |
| 2004/0015157 A1 | 1/2004 | Connors et al. | |
| 2004/0030332 A1 | 2/2004 | Knowlton et al. | |

| | | | |
|---|---|---|---|
| 2004/0034319 A1 | 2/2004 | Anderson et al. | 604/20 |
| 2004/0034341 A1 | 2/2004 | Altshuler et al. | 606/3 |
| 2004/0034346 A1 | 2/2004 | Stern et al. | |
| 2004/0039379 A1 | 2/2004 | Viator et al. | 606/9 |
| 2004/0093042 A1 | 5/2004 | Altshuler et al. | 607/88 |
| 2004/0133251 A1 | 7/2004 | Altshuler et al. | |
| 2004/0147984 A1 | 7/2004 | Altshuler et al. | |
| 2004/0162549 A1 | 8/2004 | Altshuler | |
| 2004/0199226 A1 | 10/2004 | Shadduck | |

FOREIGN PATENT DOCUMENTS

| | | |
|---|---|---|
| DE | 31 21 683 | 12/1982 |
| DE | 10082526 T1 | 7/1999 |
| DE | 201 07 271 | 7/2001 |
| EP | 0 395 307 A2 | 10/1990 |
| EP | 0 519 415 | 12/1992 |
| EP | 1 158 919 | 12/2001 |
| EP | 1 430 850 | 12/2003 |
| FR | 2 609 245 | 7/1988 |
| NZ | 266678 | 12/1997 |
| WO | 92/19414 | 11/1992 |
| WO | 93/13816 | 7/1993 |
| WO | 94/26228 | 11/1994 |
| WO | 96/27240 | 9/1996 |
| WO | 96/27327 | 9/1996 |
| WO | 96/32051 | 10/1996 |
| WO | WO 96/34568 | 11/1996 |
| WO | 96/39914 | 12/1996 |
| WO | 97/18765 | 5/1997 |
| WO | 97/18768 | 5/1997 |
| WO | WO 97/37602 | 10/1997 |
| WO | 68/03117 | 1/1998 |
| WO | 98/03220 | 1/1998 |
| WO | 98 05286 | 2/1998 |
| WO | WO 98/33558 | 8/1998 |
| WO | WO 99/08614 | 2/1999 |
| WO | WO 00/44297 | 8/2000 |
| WO | WO 00/48644 A3 | 8/2000 |
| WO | WO 00/053113 | 9/2000 |
| WO | WO 00/54685 | 9/2000 |
| WO | WO 00/54686 | 9/2000 |
| WO | WO 01/00269 | 1/2001 |
| WO | WO 01/08545 A2 | 2/2001 |
| WO | WO 02/26147 | 4/2002 |
| WO | WO 02/064209 | 8/2002 |
| WO | WO 02/076318 | 10/2002 |
| WO | WO04/086943 | 10/2004 |

OTHER PUBLICATIONS

Nelson, et al., Abstract: "Dynamic epidermal cooling during pulsed laser treatment of port-wine stain. A new methodology with preliminary clinical evaluation", *Archives of Dermatology*, 131:695-700.

Anvari, et al., "Spatially selective photocoagulation of biological tissues; feasibility study utilizing cryogen spray cooling", *Applied Optics*, vol. 35, No. 19 (Jul. 1996).

Allain, et al. "Isometric Tensions Developed During the Hydrothermal Swelling of Rat Skin", Connective Tissue Research, vol. 7, pp. 697-701, (1990).

Danielson, C. "Age-Related thermal stability and susceptibility to proteolysis of rat bone collagen", . . . chem, Great Britain, pp. 697-701, (1990).

Danielson, C. "Thermal stability of reconstituted collagin fibrils, shrinkage characteristics upon in vitro maturation", Mechanisms of Ageing and Development, vol. 15, pp. 269-278, (1981).

Kronick, et al. "The locations of collagens with different thermal stabilities in fibrils of bovine recticular dermis". Connective Tissue Research, vol. 18, pp. 123-134, (1988).

Mainster, M.A. "Ophthalmic applications of infrared lasers—thermal considerations", Visual Sci., pp. 414-420, Apr. 1979.

Pearoe, et al. "Kinetic models of laser-tissue fusion processes", ISA, paper#93-044, pp. 355-360, (1993).

Adrian, R. M. Treatment of Facial Telangiectasia Using the VersaPulse7 Variable Pulse Width Frequency Doubled Neodymium:YAG Laser: A Case Report.

Chess, C.; Chess, Q. "Cool Laser Optics Treatment of Large Telangiestasia of the Lower Extremities." *J. Dermatol Surg Oncol.* 1993; 19:74-80.

Coulson, W. F. et al. "Nonablative Laser Treatment of Facial Rhytides: Animal Study." Abstract for BiOS '98 Symposium Conference: bo05—Cutaneous Applications of Lasers, Jan. 24-30, 1998, San Jose, CA.

Kincade, K. "Demand for Laser Resurfacing Soars: Quicker Healing, Less Risk of Scarring" *Dermatology Times.* 1995. 16(10).

Fitzpatrick, R. "Treatment of Wrinkles with the UltraPhase $CO_2$ Laser."

Laser Aesthetics, Inc. "The Cool Touch Laser." Brochure.

Laser Aesthetics, Inc. "Cool Touch Model 130 Technical Specifications." Brochure.

National Health Communications, Inc. "New Laser Eliminates 'Lipstick Bleed'" Press Release Jul. 1993.

Thermage, Inc., "Complaint For Patent Infringement", Jul. 23, 2004.

Thermage, Inc., "Motion for Preliminary Injunction", Aug. 6, 2004.

Thermage, Inc., "Memorandum in Support of Motion for Preliminary Injunction", Aug. 6, 2004.

Thermage, Inc, "Declaration of Edward A. Ebbers in Support of Motion for Preliminary Injunction" and attached exhibits A-E, Aug. 6, 2004.

Thermage, Inc. "Declaration of Dr. Maureen Reitman in Support of Motion for Preliminary Injunction" and attached Exhibits A-M, Aug. 6, 2004.

Thermage, Inc. "Declaration of Dave B. Koo in Support of Motion for Preliminary Injunction" and attached Exhibits A-D, Aug. 6, 2004.

Syneron Medical, Ltd., Syneron, Inc., "Declaration of Robert S. McArthur in Support of Syneron's Opposition to Plaintiff's Motion for a Preliminary Injunction" and attached Exhibits 1-25, Aug. 17, 2004.

Syneron Medical, Ltd., Syneron, Inc., "Memorandum in Opposition to Plaintiff's Motion for a Preliminary Injunction", Aug. 27, 2004.

Syneron Medical, Ltd., Syneron, Inc., "Declaration of Dr. Warren S. Grundfest in Support of Syneron's Opposition to Plaintiff's Motion for a Preliminary Injunction" and attached Exhibits A-F, Aug. 27, 2004.

Syneron Medical, Ltd., Syneron, Inc., "Declaration of Dr. Michael Kreindel in Support of Syneron's Opposition to Plaintiff's Motion for a Preliminary Injunction" and attached Exhibit A, Aug. 27, 2004.

Syneron Medical, Ltd., Syneron, Inc., "Declaration of Domenic Serafino in Support of Syneron's Opposition to Plaintiff's Motion for a Preliminary Injunction" and attached Exhibits A-C, Aug. 27, 2004.

Syneron Medical, Ltd., Syneron, Inc., "Declaration of Moshe Mizrahy in Support of Syneron's Opposition to Plaintiff's Motion for a Preliminary Injunction", Aug. 17, 2004.

Syneron Medical, Ltd., Syneron, Inc., "Syneron Medical Ltd.'s and Syneron, Inc.'s Answer to Complaint with Jury Demand and Declaratory Judgment, Counterclaim against Thermage, Inc.", Aug. 27, 2004.

Thermage, Inc., "Reply Memorandum re Motion for Preliminary Injunction", Sep. 3, 2004.

Thermage, Inc., "Declaration of John M. Benassi in Support of Motion for Preliminary Injunction" and attached Exhibits A-B, Sep. 3, 2004.

Thermage, Inc., "Declaration of Paul Davis in Support of Motion for Preliminary Injunction" and attached Exhibits A-C, Sep. 3, 2004.

Thermage, Inc., "Declaration of Robert Gerberich in Support of Motion for Preliminary Injunction", Sep. 3, 2004.

Thermage, Inc., "Declaration of Edward W. Knowlton in Support of Motion for Preliminary Injunction", Sep. 3, 2004.

Thermage, Inc., "Declaration of Richard J. Meader in Support of Motion for Preliminary Injunction", Sep. 3, 2004.

Thermage, Inc., "Declaration of Maureen Reitman in Support of Motion for Preliminary Injunction (Supplemental)", Sep. 3, 2004.

Syneron Medical, Ltd., Syneron, Inc., "Motion for Leave to File Syneron's Surreply in Opposition to Preliminary Injunction Motion", Sep. 10, 2004.

Syneron Medical, Ltd., Syneron, Inc., "Surreply in Opposition to Thermage, Inc.'s Preliminary Injunction Motion", Sep. 10, 2004.

Syneron Medical, Ltd., Syneron, Inc., "Supplemental Declaration of Jill Neiman in Opposition to Preliminary Injunction Motion" and attached Exhibits A-C, Sep. 10, 2004.

Syneron Medical, Ltd., Syneron, Inc., "Supplemental Declaration of Warren Grundfest in Opposition to Preliminary Injunction Motion" and attached Exhibits A-B, Sep. 10, 2004.

Judge Charles R. Breyer, "Order granting Motion for Leave to File Surreply", Sep. 13, 2004.

Thermage, Inc., "Memorandum in Opposition re Motion for Preliminary Injunction to Syneron's Surreply", Sep. 14, 2004.

Judge Charles R. Breyer, "Order Regarding Questions for Oral Argument", Sep. 16, 2004.

Thermage, Inc., "Answer to CounterClaim", Sep. 16, 2004.

Themage, Inc., "Minute Entry: Motion Hearing held on Sep. 17, 2004 before Judge Charles R. Breyer re Motion for Preliminary Injunction", Sep. 17, 2004.

Judge Charles R. Breyer, "Order denying Motion for Preliminary Injunction", Sep. 27, 2004.

Judge Charles R. Breyer, "Transcript of Proceedings held on Sep. 17, 2004", Oct. 8, 2004.

Anvari et al., "Dynamic Epidermal Cooling in Conjunction with Laser Treatment of Port-Wine Stains: Theoretical and Preliminary Clinical Evaluations," Lasers in Medical Studies, 10: 105-112, 1995.

Anvari et al., "Spatially Selective Photocoagulation of Biological Tissues: Feasibility Study Utilizing Cryogen Spray Cooling," Applied Optics, vol. 35, No. 19, Jul. 1, 1996.

* cited by examiner

HANDPIECE FOR TREATMENT OF TISSUE

CROSS-RELATED TO RELATED APPLICATIONS

This application is a continuation-in-part of U.S. Ser. No. 09/522,275, filed Mar. 9, 2000, now U.S. Pat. No. 6,413,255, which claims the benefit of U.S. Application No. 60/123,440, filed Mar. 9, 1999, both of which are fully incorporated herein by reference.

FIELD OF THE INVENTION

This invention relates generally to a handpiece for treating tissue, and more particularly, to an RF electrode handpiece for treating skin and underlying tissues.

DESCRIPTION OF RELATED ART

The human skin is composed of two elements: the epidermis and the underlying dermis. The epidermis with the stratum corneum serves as a biological barrier to the environment. In the basilar layer of the epidermis, pigment-forming cells called melanocytes are present. They are the main determinants of skin color.

The underlying dermis provides the main structural support of the skin. It is composed mainly of an extra-cellular protein called collagen. Collagen is produced by fibroblasts and synthesized as a triple helix with three polypeptide chains that are connected with heat labile and heat stable chemical bonds. When collagen-containing tissue is heated, alterations in the physical properties of this protein matrix occur at a characteristic temperature. The structural transition of collagen contraction occurs at a specific "shrinkage" temperature. The Collagen crosslinks are either intramolecular (covalent or hydrogen bond) or intermolecular (covalent or ionic bonds). The thermal cleavage of intramolecular hydrogen crosslinks is a scalar process that is created by the balance between cleavage events and relaxation events (reforming of hydrogen bonds). No external force is required for this process to occur. As a result, intermolecular stress is created by the thermal cleavage of intramolecular hydrogen bonds. Essentially, the contraction of the tertiary structure of the molecule creates the initial intermolecular vector of contraction.

Collagen fibrils in a matrix exhibit a variety of spatial orientations. The matrix is lengthened if the sum of all vectors acts to distract the fibril. Contraction of the matrix is facilitated if the sum of all extrinsic vectors acts to shorten the fibril. Thermal disruption of intramolecular hydrogen bonds and mechanical cleavage of intermolecular crosslinks is also affected by relaxation events that restore preexisting configurations. However, a permanent change of molecular length will occur if crosslinks are reformed after lengthening or contraction of the collagen fibril. The continuous application of an external mechanical force will increase the probability of crosslinks forming after lengthening or contraction of the fibril.

Hydrogen bond cleavage is a quantum mechanical event that requires a threshold of energy. The amount of (intramolecular) hydrogen bond cleavage required corresponds to the combined ionic and covalent intermolecular bond strengths within the collagen fibril. Until this threshold is reached, little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and nonpolar regions in the lengthened or contracted fibril.

Cleavage of collagen bonds also occurs at lower temperatures but at a lower rate. Low-level thermal cleavage is frequently associated with relaxation phenomena in which bonds are reformed without a net change in molecular length. An external force that mechanically cleaves the fibril will reduce the probability of relaxation phenomena and provides a means to lengthen or contract the collagen matrix at lower temperatures while reducing the potential of surface ablation.

Soft tissue remodeling is a biophysical phenomenon that occurs at cellular and molecular levels. Molecular contraction or partial denaturization of collagen involves the application of an energy source, which destabilizes the longitudinal axis of the molecule by cleaving the heat labile bonds of the triple helix. As a result, stress is created to break the intermolecular bonds of the matrix. This is essentially an immediate extra-cellular process, whereas cellular contraction requires a lag period for the migration and multiplication of fibroblasts into the wound as provided by the wound healing sequence. In higher developed animal species, the wound healing response to injury involves an initial inflammatory process that subsequently leads to the deposition of scar tissue.

The initial inflammatory response consists of the infiltration by white blood cells or leukocytes that dispose of cellular debris. Seventy-two hours later, proliferation of fibroblasts at the injured site occurs. These cells differentiate into contractile myofibroblasts, which are the source of cellular soft tissue contraction. Following cellular contraction, collagen is laid down as a static supporting matrix in the tightened soft tissue structure. The deposition and subsequent remodeling of this nascent scar matrix provides the means to alter the consistency and geometry of soft tissue for aesthetic purposes.

In light of the preceding discussion, there are a number of dermatological procedures that lend themselves to treatments which deliver thermal energy to the skin and underlying tissue to cause a contraction of collagen, and/or initiate a would healing response. Such procedures include skin remodeling/resurfacing, wrinkle removal, and treatment of the sebaceous glands, hair follicles adipose tissue and spider veins. Currently available technologies that deliver thermal energy to the skin and underlying tissue include Radio Frequency (RF), optical (laser) and other forms of electromagnetic energy. However, these technologies have a number of technical limitations and clinical issues which limit the effectiveness of the treatment and/or preclude treatment altogether. These issues include the following: i) achieving a uniform thermal effect across a large area of tissue, ii) controlling the depth of the thermal effect to target selected tissue and prevent unwanted thermal damage to both target and non-target tissue, iii) reducing adverse tissue effects such as burns, redness blistering, iv) replacing the practice of delivery energy/treatment in a patchwork fashion with a more continuous delivery of treatment (e.g. by a sliding or painting motion), v) improving access to difficult-to-reach areas of the skin surface and vi) reducing procedure time and number of patient visits required to complete treatment. As will be discussed herein the current invention provides an apparatus for solving these and other limitations.

One of the key shortcomings of currently available RF technology for treating the skin is the edge effect phenomenon. In general, when RF energy is being applied or delivered to tissue through an electrode which is in contact with that tissue, the current patterns concentrate around the edges of the electrode, sharp edges in particular. This effect is generally known as the edge effect. In the case of a circular disc electrode, the effect manifests as a higher current density around the perimeter of that circular disc and a relatively low current density in the center. For a square-shaped electrode there is typically a high current density around the entire perimeter, and an even higher current density at the corners where there is a sharp edge.

Edge effects cause problems in treating the skin for several reasons. First, they result in a non-uniform thermal effect over the electrode surface. In various treatments of the skin, it is important to have a uniform thermal effect over a relatively large surface area, particularly for dermatologic treatments. Large in this case being on the order of several square millimeters or even several square centimeters. In electrosurgical applications for cutting tissue, there typically is a point type applicator designed with the goal of getting a hot spot at that point for cutting or even coagulating tissue. However, this point design is undesirable for creating a reasonably gentle thermal effect over a large surface area. What is needed is an electrode design to deliver uniform thermal energy to skin and underlying tissue without hot spots.

A uniform thermal effect is particularly important when cooling is combined with heating in skin/tissue treatment procedure. As is discussed below, a non-uniform thermal pattern makes cooling of the skin difficult and hence the resulting treatment process as well. When heating the skin with RF energy, the tissue at the electrode surface tends to be warmest with a decrease in temperature moving deeper into the tissue. One approach to overcome this thermal gradient and create a thermal effect at a set distance away from the electrode is to cool the layers of skin that are in contact with the electrode. However, cooling of the skin is made difficult if there is a non-uniform heating pattern. If the skin is sufficiently cooled such that there are no burns at the corners of a square or rectangular electrode, or at the perimeter of a circular disc electrode, then there will probably be overcooling in the center and there won't be any significant thermal effect (i.e. tissue heating) under the center of the electrode. Contrarily, if the cooling effect is decreased to the point where there is a good thermal effect in the center of the electrode, then there probably will not be sufficient cooling to protect tissue in contact with the edges of the electrode. As a result of these limitations, in the typical application of a standard electrode there is usually an area of non-uniform treatment and/or burns on the skin surface. So uniformity of the heating pattern is very important. It is particularly important in applications treating skin where collagen-containing layers are heated to produce a collagen contraction response for tightening of the skin. For this and related applications, if the collagen contraction and resulting skin tightening effect are non-uniform, then a medically undesirable result may occur.

There is a need for an improved RF handpiece for cosmetic applications.

SUMMARY OF THE INVENTION

Accordingly, an object of the present invention is to provide an RF handpiece which provides a substantially uniform delivery of energy to a target tissue site.

Another object of the present invention is to provide an RF handpiece which includes at least one RF electrode that is capacitively coupled to a skin surface when at least a portion of the RF electrode is in contact with the skin surface.

Yet another object of the present invention is to provide an RF handpiece that provides a uniform thermal effect in tissue at a selected depth, while preventing or minimizing thermal damage to a skin surface and other non-target tissue.

A further object of the present invention is to provide an RF handpiece configured to reduce or eliminate the edge effects and hot spots of RF electrodes applied to skin surfaces.

Another object of the present invention is to provide an RF handpiece configured to provide an atomizing delivery of a cooling fluidic medium to the RF electrode.

Still another object of the present invention is to provide an RF handpiece configured to evaporatively cool the back surface of the RF electrode, and conductively cool a skin surface adjacent to a front surface of the RF electrode.

A further object of the present invention is to provide an RF handpiece configured to controllably deliver a cooling fluidic medium to the back surface of the RF electrode at substantially any orientation of the front surface of the RF electrode relative to a direction of gravity.

Yet another object of the present invention is to provide an RF handpiece that includes an RF electrode with both conductive and dielectric portions.

Another object of the present invention is to provide an RF handpiece that includes a force sensor that zeros out gravity effects created by the weight of the electrode assembly of the RF handpiece in any orientation of the front surface of the RF electrode relative to a direction of gravity.

These and other objects of the present invention are achieved in a handpiece that has a handpiece assembly. The handpiece assembly includes a handpiece housing and a cooling fluidic medium valve member. An electrode assembly is coupled to the handpiece housing. The electrode assembly has a least one RF electrode that is capacitively coupled to a skin surface when at least a portion of the RF electrode is in contact with the skin surface.

In another embodiment of the present invention a handpiece, a handpiece assembly includes a handpiece housing and a cooling fluidic medium valve member with an inlet and an outlet. An electrode assembly is removeably coupled to the handpiece housing. The electrode assembly has a least one RF electrode with a front surface and a back surface. The RF electrode is capacitively coupled to a skin surface when at least a portion of the RF electrode is in contact with the skin surface.

In another embodiment of the present invention, a handpiece includes a handpiece assembly with a handpiece housing. An insert is at least partially positionable in the handpiece housing. An RF electrode is coupled to the insert. The RF electrode has a back surface that faces the handpiece housing and an opposing front surface. A cooling fluidic medium dispensing assembly is coupled to the handpiece housing and the insert.

In another embodiment of the present invention, a handpiece includes a handpiece assembly with a handpiece housing. An insert is detachably coupled to the handpiece housing. The insert includes an RF electrode with a conductive portion and a dielectric.

In another embodiment of the present invention, a handpiece includes a handpiece assembly with a handpiece housing. An insert is detachably coupled to the handpiece housing. An RF electrode is positioned in the insert. The RF electrode includes a flex circuit.

In another embodiment of the present invention, a handpiece includes a handpiece assembly with a handpiece housing. An insert is detachably coupled to the handpiece housing. The insert includes a flex circuit and an RF electrode that with a conductive portion and a dielectric.

DETAILED DESCRIPTION

Figure 1:
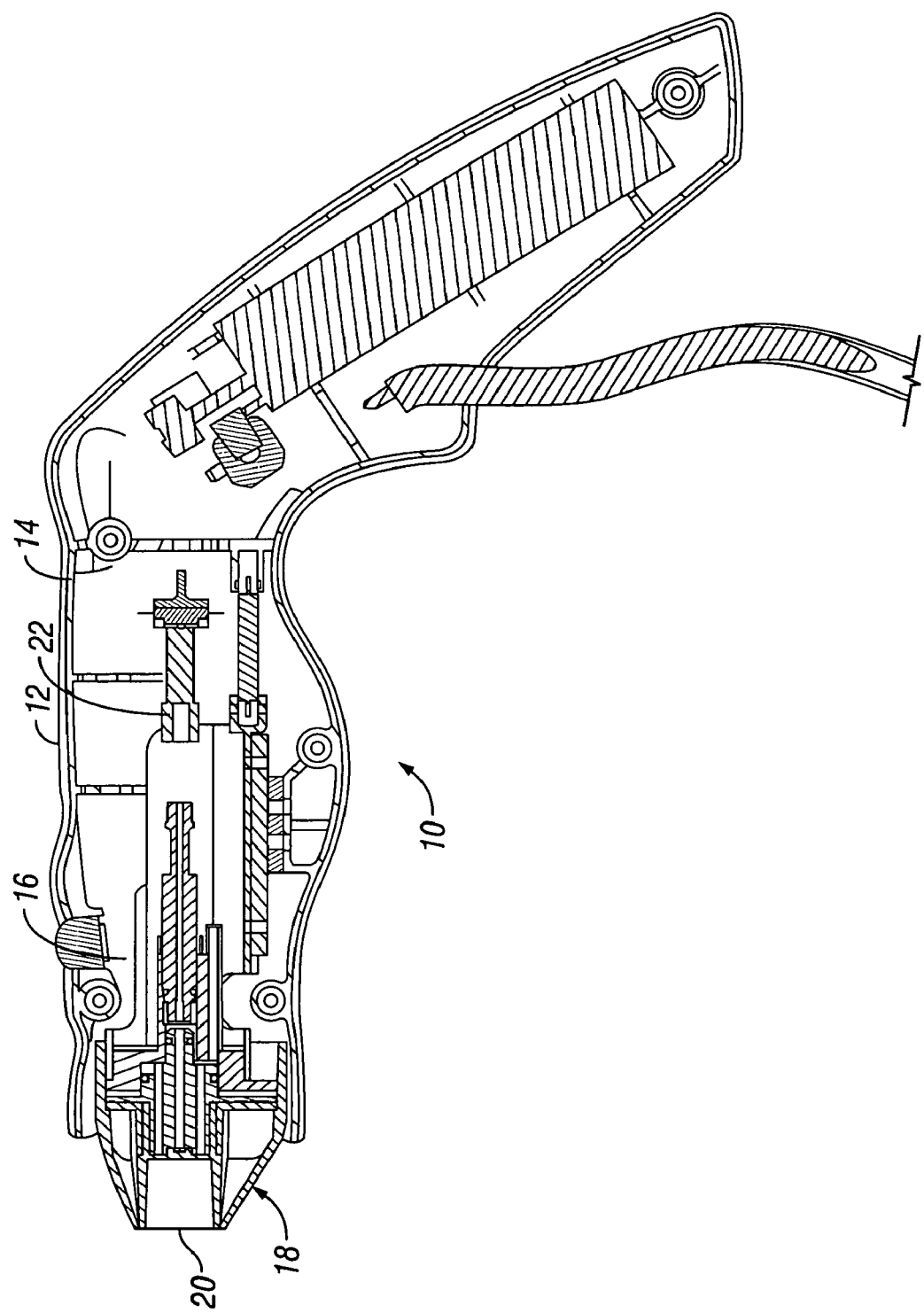
FIG. 1 is a cross-sectional view of one embodiment of the handpiece of the present invention.

Referring now to FIG. 1, one embodiment of the present invention is a handpiece 10 with a handpiece assembly 12. Handpiece assembly 12 includes a handpiece housing 14 and a cooling fluidic medium valve member 16. An electrode assembly 18 is coupled to handpiece housing 14. Electrode assembly 18 has a least one RF electrode 20 that is capacitively coupled to a skin surface when at least a portion of RF electrode 20 is in contact with the skin surface. Without limiting the scope of the present invention, RF electrode 20 can have a thickness in the range of 0.010 to 1.0 mm.

Handpiece 10 provides a more uniform thermal effect in tissue at a selected depth, while preventing or minimizing thermal damage to the skin surface and other non-target tissue. Handpiece 10 is coupled to an RF generator. RF electrode 20 can be operated either in mono-polar or bi-polar modes. Handpiece 10 is configured to reduce, or preferably eliminate edge effects and hot spots. The result is an improved aesthetic result/clinical outcome with an elimination/reduction in adverse effects and healing time.

A fluid delivery member 22 is coupled to cooling fluidic medium valve member 16. Fluid delivery member 22 and cooling fluidic medium valve member 16 collectively form a cooling fluidic medium dispensing assembly. Fluid delivery member 16 is configured to provide an atomizing delivery of a cooling fluidic medium to RF electrode 20. The atomizing delivery is a mist or fine spray. A phase transition, from liquid to gas, of the cooling fluidic medium occurs when it hits the surface of RF electrode 20. The transition from liquid to gas creates the cooling. If the transition before the cooling fluidic medium hits RF electrode 20 the cooling of RF electrode 20 will not be as effective.

In one embodiment, the cooling fluidic medium is a cryogenic spray, commercially available from Honeywell, Morristown, N.J. A specific example of a suitable cryogenic spray is R134A$_2$, available from Refron, Inc., 38-18 33$^{rd}$ St, Long Island City, N.Y. 11101. The use of a cryogenic cooling fluidic medium provides the capability to use a number of different types of algorithms for skin treatment. For example, the cryogenic cooling fluidic medium can be applied milliseconds before and after the delivery of RF energy to the desired tissue. This is achieved with the use of cooling fluidic medium valve member 16 coupled to a cryogen supply, including but not limited to a compressed gas canister. In various embodiments, cooling fluidic medium valve member 16 can be coupled to a computer control system and/or manually controlled by the physician by means of a foot switch or similar device.

A key advantage of providing a spray, or atomization, of cryogenic cooling fluidic medium is the availability to implement rapid on and off control. Cryogenic cooling fluidic medium allows more precise temporal control of the cooling process. This is because cooling only occurs when the refrigerant is sprayed and is in an evaporative state, the latter being a very fast short-lived event. Thus, cooling ceases rapidly after the cryogenic cooling fluidic medium is stopped. The overall effect is to confer very precise time on-off control of cryogenic cooling fluidic medium.

Figure 2:
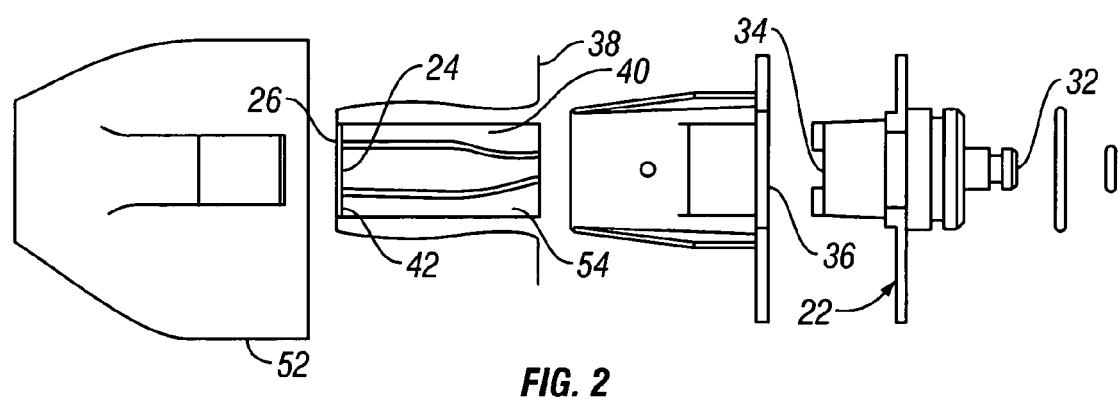
FIG. 2 is an exploded view of the FIG. 1 insert assembly.

Referring now to FIG. 2, fluid delivery member 22 can be positioned in handpiece housing 14 or electrode assembly 18. Fluid delivery member 22 is configured to controllably deliver a cooling fluidic medium to a back surface 24 of RF electrode 20 and maintain back surface 24 at a desired temperature. The cooling fluidic medium evaporatively cools RF electrode 20 and maintains a substantially uniform temperature of front surface 26 of RF electrode 20. Front surface 26 can be sufficiently flexible and conformable to the skin, but still have sufficient strength and/or structure to provide good thermal coupling when pressed against the skin surface.

RF electrode 20 then conductively cools a skin surface that is adjacent to a front surface 26 of RF electrode 20. Suitable fluidic media include a variety of refrigerants such as R134A and freon. Fluid delivery member 22 is configured to controllably deliver the cooling fluidic medium to back surface 24 at substantially any orientation of front surface 26 relative to a direction of gravity. A geometry and positioning of fluid delivery member 22 are selected to provide a substantially uniform distribution of cooling fluidic medium on back surface 24. The delivery of the cooling fluidic medium can be by spray of droplets or fine mist, flooding back surface 24, and the like. Cooling occurs at the interface of the cooling fluidic medium with atmosphere, which is where evaporation occurs. If there is a thick layer of fluid on back surface 24 the heat removed from the treated skin will need to pass through the thick layer of cooling fluidic medium, increasing thermal resistance. To maximize cooling rates, it is desirable to apply a very thin layer of cooling fluidic medium. If RF electrode 20 is not horizontal, and if there is a thick layer of cooling fluidic medium, or if there are large drops of cooling fluidic medium on back surface 24, the cooling fluidic medium can run down the surface of RF electrode 20 and pool at one edge or corner, causing uneven cooling. Therefore, it is desirable to apply a thin layer of cooling fluidic medium with a fine spray.

Figure 3:
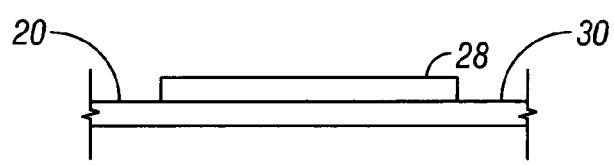
FIG. 3 is a close-up view of one embodiment of an RF electrode of the present invention.

In various embodiments, RF electrode 20, as illustrated in FIG. 3, has a conductive portion 28 and a dielectric portion 30. Conductive portion 28 can be a metal including but not limited to copper, gold, silver, aluminum and the like. Dielectric portion 30 can be made of a variety of different materials including but not limited to polyimide, and the like. Other dielectric materials include but are not limited to silicon, sapphire, diamond, zirconium-toughened alumina (ZTA), alumina and the like. Dielectric portion 30 can be positioned around at least a portion, or the entirety of a periphery of conductive portion 28. Suitable materials for a dielectric portion 30 include, but are not limited to, Teflon® and the like, silicon nitride, polysilanes, polysilazanes, polyimides, Kapton and other polymers, antenna dielectrics and other dielectric materials well known in the art. In another embodiment, RF electrode 20 is made of a composite material, including but not limited to gold-plated copper, copper-polyimide, silicon/silicon-nitride and the like.

Dielectric portion 30 creates an increased impedance to the flow of electrical current through RF electrode 20. This increased impedance causes current to travel a path straight down through conductive portion 28 to the skin surface. Electric field edge effects, caused by a concentration of current flowing out of the edges of RF electrode 20, are reduced.

Dielectric portion 30 produces a more uniform impedance through RF electrode 20 and causes a more uniform current to flow through conductive portion 28. The resulting effect minimizes or even eliminates, edge effects around the edges of RF electrode 20.

In one embodiment, conductive portion 28 adheres to dielectric portion 30 which can be substrate with a thickness, by way of example and without limitation, of about 0.001". This embodiment is similar to a standard flex circuit board material commercially available in the electronics industry. In this embodiment, dielectric portion 30 is in contact with the tissue, the skin, and conductive portion 28 is separated from the skin. The thickness of the dielectric portion 30 can be decreased by growing conductive portion 28 on dielectric portion 30 using a variety of techniques, including but not limited to, sputtering, electro deposition, chemical vapor deposition, plasma deposition and other deposition techniques known in the art. Additionally, these same processes can be used to deposit dielectric portion 30 onto conductive portion 28. In one embodiment dielectric portion 30 is an oxide layer which can be grown on conductive portion 28. An oxide layer has a low thermal resistance and improves the cooling efficiency of the skin compared with many other dielectrics such as polymers.

Fluid delivery member 22 has an inlet 32 and an outlet 34. Outlet 34 can have a smaller cross-sectional area than a cross-sectional area of inlet 32. In one embodiment, fluid delivery member 22 is a nozzle 36.

Cooling fluidic medium valve member 16 can be configured to provide a pulsed delivery of the cooling fluidic medium. Pulsing the delivery of cooling fluidic medium is a simple way to control the rate of cooling fluidic medium application. In one embodiment, cooling fluidic medium valve member 16 is a solenoid valve. An example of a suitable solenoid valve is a solenoid pinch valve manufactured by the N-Research Corporation, West Caldwell, N.J. If the fluid is pressurized, then opening of the valve results in fluid flow. If the fluid is maintained at a constant pressure, then the flow rate is constant and a simple open/close solenoid valve can be used, the effective flow rate being determined by the pulse duty cycle. A higher duty cycle, close to 100% increases cooling, while a lower duty cycle, closer to 0%, reduces cooling. The duty cycle can be achieved by turning on the valve for a short duration of time at a set frequency. The duration of the open time can be 1 to 50 milliseconds or longer. The frequency of pulsing can be 1 to 50 Hz or faster.

Alternatively, cooling fluidic medium flow rate can be controlled by a metering valve or controllable-rate pump such as a peristaltic pump. One advantage of pulsing is that it is easy to control using simple electronics and control algorithms.

Electrode assembly 18 is sufficiently sealed so that the cooling fluidic medium does not leak from back surface 24 onto a skin surface in contact with a front surface of RF electrode 20. This helps provide an even energy delivery through the skin surface. In one embodiment, electrode assembly 18, and more specifically RF electrode 20, has a geometry that creates a reservoir at back surface 24 to hold and gather cooling fluidic medium that has collected at back surface 24. Back surface 24 can be formed with "hospital corners" to create this reservoir. Optionally, electrode assembly 18 includes a vent 38 that permits vaporized cooling fluidic medium to escape from electrode assembly 18. This reduces the chance of cooling fluidic medium collecting at back surface 24. This can occur when cooling fluidic medium is delivered to back surface 24 in vapor form and then, following cooling of back surface 24, the vapor condenses to a liquid.

Vent 38 prevents pressure from building up in electrode assembly 18. Vent 38 can be a pressure relief valve that is vented to the atmosphere or a vent line. When the cooling fluidic medium comes into contact with RF electrode 20 and evaporates, the resulting gas pressurizes the inside of electrode assembly 18. This can cause RF electrode 20 to partially inflate and bow out from front surface 26. The inflated RF electrode 20 can enhance the thermal contact with the skin and also result in some degree of conformance of RF electrode 20 to the skin surface. An electronic controller can be provided. The electronic controller sends a signal to open vent 38 when a programmed pressure has been reached.

Various leads 40 are coupled to RF electrode 20. One or more thermal sensors 42 are coupled to RF electrode. Suitable thermal sensors 42 include but are not limited to thermocouples, thermistors, infrared photo-emitters and a thermally sensitive diode. In one embodiment, a thermal sensor 42 is positioned at each corner of RF electrode 20. A sufficient number of thermal sensors 42 are provided in order to acquire sufficient thermal data of the skin surface. Thermal sensors 42 are electrically isolated from RF electrode 20.

Thermal sensors 42 measure temperature and can provide feedback for monitoring temperature of Rf electrode 20 and/or the tissue during treatment. Thermal sensors 42 can be thermistors, thermocouples, thermally sensitive diodes, capacitors, inductors or other devices for measuring temperature. Preferably, thermal sensors 42 provide electronic feedback to a microprocessor of the an RF generator coupled to RF electrode 20 in order to facilitate control of the treatment.

The measurements from thermal sensors 42 can be used to help control the rate of application of cooling fluidic medium. For example, the cooling control algorithm can be used to apply cooling fluidic medium to RF electrode 20 at a high flow rate until the temperature fell below a target temperature, and then slow down or stop. A PID, or proportional-integral-differential, algorithm can be used to precisely control RF electrode 20 temperature to a predetermined value.

Thermal sensors 42 can be positioned placed on back surface 24 of RF electrode 20 away from the tissue. This configuration is preferable ideal for controlling the temperature of the RF electrode 20. Alternatively, thermal sensors 42 can be positioned on front surface 26 of RF electrode 10 in direct contact with the tissue. This embodiment can be more suitable for monitoring tissue temperature. Algorithms are utilized with thermal sensors 42 to calculate a temperature profile of the treated tissue. Thermal sensors 42 can be used to develop a temperature profile of the skin which is then used for process control purposes to assure that the proper amounts of heating and cooling are delivered to achieve a desired elevated deep tissue temperature while maintaining skin tissue layers below a threshold temperature and avoid thermal injury. The physician can use the measured temperature profile to assure that he stays within the boundary of an ideal/average profile for a given type of treatment. Thermal sensors 42 can be used for additional purposes. When the temperature of thermal sensors 42 is monitored it is possible to detect when RF electrode 20 is in contact with the skin surface. This can be achieved by detecting a direct change in temperature when skin contact is made or examining the rate of change of temperature which is affected by contact with the skin. Similarly, if there is more than one thermal sensor 42, the thermal sensors 42 can be used to detect whether a portion of RF electrode 20 is lifted or out of contact with skin. This can be important because the current density (amperes per unit area) delivered to the skin can vary if the contact area changes. In particular, if part of the surface of RF electrode 20 is not in contact with the skin, the resulting current density is higher than expected.

Figure 4:
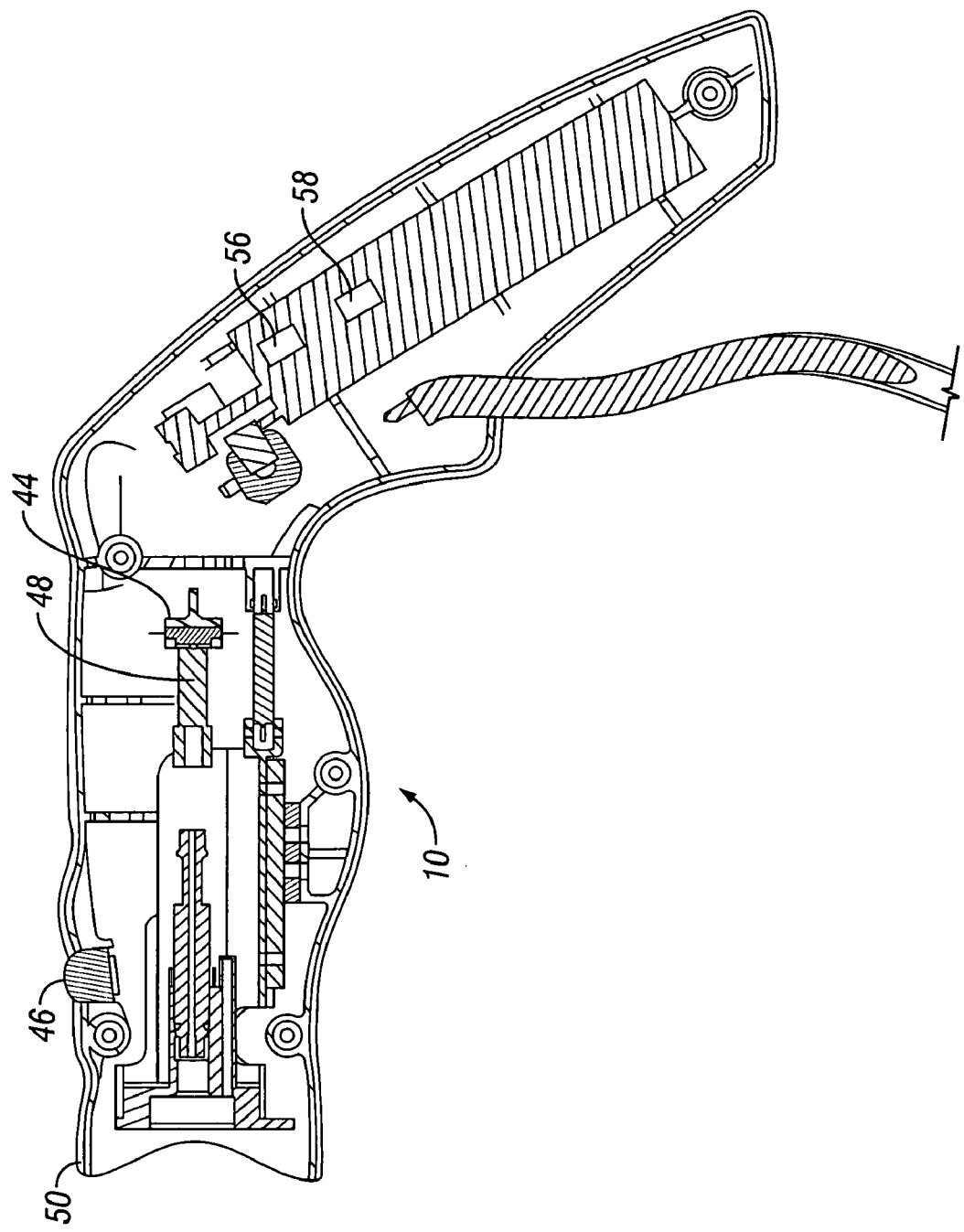
FIG. 4 is another cross-sectional view of a portion of the handpiece housing from FIG. 1.

Referring now to FIG. 4, a force sensor 44 is also coupled to electrode assembly 18. Force sensor 44 detects an amount of force applied by electrode assembly 18, via the physician, against an applied skin surface. Force sensor 44 zeros out gravity effects of the weight of electrode assembly 18 in any orientation of front surface 26 of RF electrode 20 relative to a direction of gravity. Additionally, force sensor 44 provides an indication when RF electrode 20 is in contact with a skin surface. Force sensor 44 also provides a signal indicating that a force applied by RF electrode 20 to a contacted skin surface is, (i) below a minimum threshold or (ii) above a maximum threshold.

An activation button 46 is used in conjunction with the force sensor. Just prior to activating Rf electrode 20, the physician holds handpiece 10 in position just off the surface of the skin. The orientation of handpiece 10 can be any angle relative to the angle of gravity. To arm handpiece 10, the physician can press activation button 46 which tares force sensor 44, by setting it to read zero. This cancels the force due to gravity in that particular treatment orientation. This method allows consistent force application of RF electrode 20 to the skin surface regardless of the angle of handpiece 10 relative to the direction of gravity.

RF electrode 20 can be a flex circuit, which can include trace components. Additionally, thermal sensor 42 and force sensor 44 can be part of the flex circuit. Further, the flex circuit can include a dielectric that forms a part of RF electrode 20.

Figure 5:
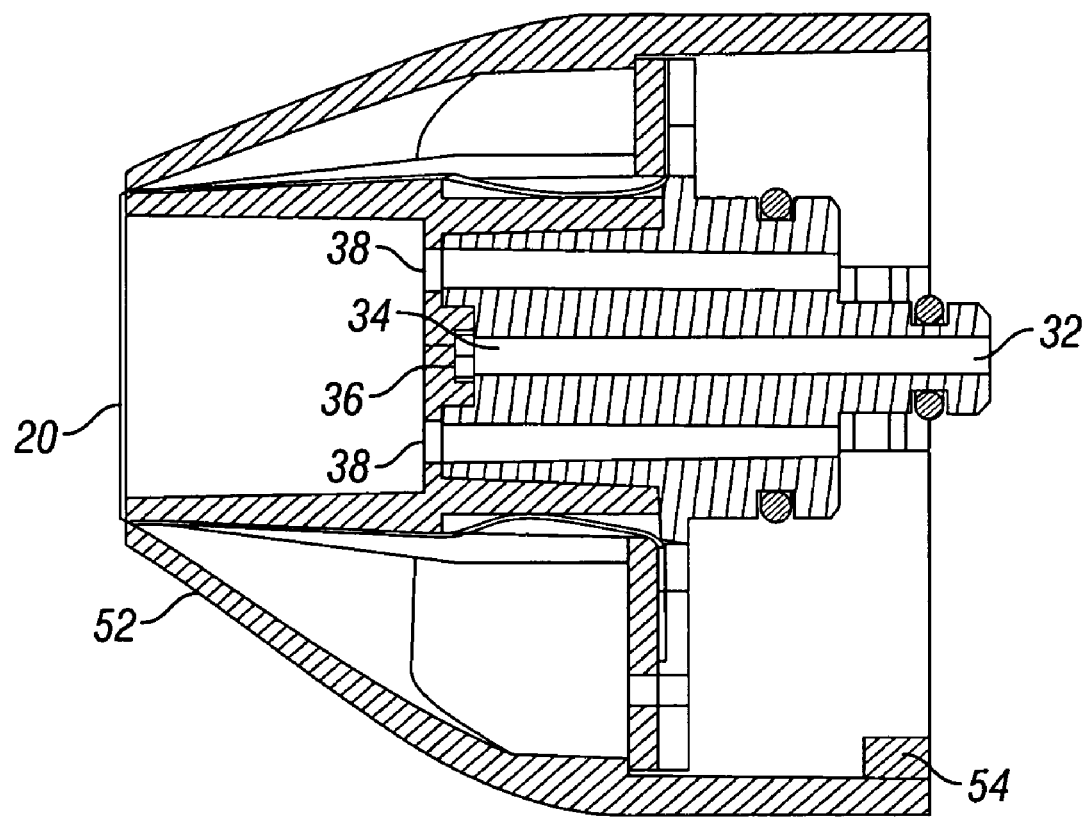
FIG. 5 is a cross-sectional view of the insert from FIG. 1.

Electrode assembly 18 can be moveable positioned within handpiece housing 12. In one embodiment, electrode assembly 18 is slideably moveable along a longitudinal axis of handpiece housing 12. Electrode assembly 18 can be rotatably mounted in handpiece housing 12. Additionally, RF electrode 20 can be rotatably positioned in electrode assembly 18. Electrode assembly 18 can be removably coupled to handpiece housing 12 as a disposable or non-disposable insert 52, see FIG. 5. For purposes of this disclosure, electrode assembly 18 is the same as insert 52. Once movably mounted to handpiece housing 12, insert 52 can be coupled to handpiece housing 12 via force sensor 44. Force sensor 44 can be of the type that is capable of measuring both compressive and tensile forces. In other embodiments, force sensor 44 only measures compressive forces, or only measures tensile forces.

Insert 52 can be spring-loaded with a spring 48. In one embodiment, spring 48 biases RF electrode 20 in a direction toward handpiece housing 12. This pre-loads force sensor 44 and keeps insert 52 pressed against force sensor 44. The pre-load force is tared when activation button 46 is pressed just prior to application of RF electrode 20 to the skin surface.

A shroud 50 is optionally coupled to handpiece 10. Shroud 50 serves to keep the user from touching insert 52 during use which can cause erroneous force readings.

A non-volatile memory 54 can be included with insert 52. Additionally, non-volatile memory can be included with handpiece housing 12. Non-volatile memory 54 can be an EPROM and the like. Additionally, a second non-volatile memory 56 can be included in handpiece housing 12 for purposes of storing handpiece 10 information such as but not limited to, handpiece model number or version, handpiece software version, number of RF applications that handpiece 10 has delivered, expiration date and manufacture date. Handpiece housing 12 can also contain a microprocessor 58 for purposes of acquiring and analyzing data from various sensors on handpiece housing 12 or insert 52 including but not limited to thermal sensors 42 force sensors 44, fluid pressure gauges, switches, buttons and the like. Microprocessor 58 can also control components on handpiece 10 including but not limited to lights, LEDs, valves, pumps or other electronic components. Microprocessor 58 can also communicate data to a microprocessor of the RF generator.

Non-volatile memory 54 can store a variety of data that can facilitate control and operation of handpiece 10 and its associated system including but not limited to, (i) controlling the amount of current delivered by RF electrode 20, (ii) controlling the duty cycle of the fluid delivery member 22, (iii) controlling the energy delivery duration time of the RF electrode 20, (iv) controlling the temperature of RF electrode 20 relative to a target temperature, (v) providing a maximum number of firings of RF electrode 20, (vi) providing a maximum allowed voltage that is deliverable by RF electrode 20, (vii) providing a history of RF electrode 20 use, (viii) providing a controllable duty cycle to fluid delivery member 22 for the delivery of the cooling fluidic medium to back surface 24 of RF electrode 20, (ix) providing a controllable delivery rate of cooling fluidic medium delivered from fluid delivery member 22 to back surface 24, and the like.

Handpiece 10 can be used to deliver thermal energy to modify tissue including, but not limited to, collagen containing tissue, in the epidermal, dermal and subcutaneous tissue layers, including adipose tissue. The modification of the tissue includes modifying a physical feature of the tissue, a structure of the tissue or a physical property of the tissue. The modification can be achieved by delivering sufficient energy to cause collagen shrinkage, and/or a wound healing response including the deposition of new or nascent collagen.

Handpiece 10 can be utilized for performing a number of treatments of the skin and underlying tissue including but not limited to, (i) dermal remodeling and tightening, (ii) wrinkle reduction, (iii) elastosis reduction, (iv) sebaceous gland removal/deactivation, (v) hair follicle removal, (vi) adipose tissue remodeling/removal, (vii) spider vein removal, and the like.

In various embodiments, handpiece 10 can be utilized in a variety of treatment processes, including but not limited to, (i) pre-cooling, before the delivery of energy to the tissue has begun, (ii) an on phase or energy delivery phase in conjunction with cooling and (iii) post cooling after the delivery of energy to tissue has stopped.

Handpiece 10 can be used to pre-cool the surface layers of the target tissue so that when RF electrode 20 is in contact with the tissue, or prior to turning on the RF energy source, the superficial layers of the target tissue are already cooled. When RF energy source is turned on or delivery of RF to the tissue otherwise begins, resulting in heating of the tissues, the tissue that has been cooled is protected from thermal effects including thermal damage. The tissue that has not been cooled will warm up to therapeutic temperatures resulting in the desired therapeutic effect.

Pre-cooling gives time for the thermal effects of cooling to propagate down into the tissue More specifically, pre-cooling allows the achievement of a desired tissue depth thermal profile, with a minimum desired temperature being achieved at a selectable depth. The amount or duration of pre-cooling can be used to select the depth of the protected zone of untreated tissue. Longer durations of pre-cooling produce a deeper protected zone and hence a deeper level in tissue for the start of the treatment zone. The opposite is true for shorter periods of pre-cooling. The temperature of front surface 26 of RF electrode 20 also affects the temperature profile. The colder the temperature of front surface 26, the faster and deeper the cooling, and vice verse.

Post-cooling can be important because it prevents and/or reduces heat delivered to the deeper layers from conducting upward and heating the more superficial layers possibly to therapeutic or damaging temperature range even though external energy delivery to the tissue has ceased. In order to prevent this and related thermal phenomena, it can be desirable to maintain cooling of the treatment surface for a period of time after application of the RF energy has ceased. In various embodiments, varying amounts of post cooling can be combined with real-time cooling and/or pre-cooling.

In various embodiments, handpiece 10 can be used in a varied number of pulse on-off type cooling sequences and algorithms may be employed. In one embodiment, the treatment algorithm provides for pre-cooling of the tissue by starting a spray of cryogenic cooling fluidic medium, followed by a short pulse of RF energy into the tissue. In this embodiment, the spray of cryogenic cooling fluidic medium continues while the RF energy is delivered, and is stopping shortly thereafter, e.g. on the order of milliseconds. This or another treatment sequence can be repeated again. Thus in various embodiments, the treatment sequence can include a pulsed sequence of cooling on, heat, cooling off, cooling on, heat, cool off, and with cooling and heating durations on orders of tens of milliseconds. In these embodiments, every time the surface of the tissue of the skin is cooled, heat is removed from the skin surface. Cryogenic cooling fluidic medium spray duration, and intervals between sprays, can be in the tens of milliseconds ranges, which allows surface cooling while still delivering the desired thermal effect into the deeper target tissue.

In various embodiments, the target tissue zone for therapy, also called therapeutic zone or thermal effect zone, can be at a tissue depth from approximately 100 μm beneath the surface of the skin down to as deep as 10 millimeters, depending upon the type of treatment. For treatments involving collagen contraction, it can be desirable to cool both the epidermis and the superficial layers of the dermis of the skin that lies beneath the epidermis, to a cooled depth range between 100 μm two millimeters. Different treatment algorithms can incorporate different amounts of pre-cooling, heating and post cooling phases in order to produce a desired tissue effect at a desired depth.

Various duty cycles, on and off times, of cooling and heating are utilized depending on the type of treatment. The cooling and heating duty cycles can be controlled and dynamically varied by an electronic control system known in the art. Specifically the control system can be used to control cooling fluidic medium valve member 16 and the RF power source.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A handpiece for non-invasively treating tissue using RF energy, comprising:
    a handpiece assembly including a handpiece housing; and
    an electrode assembly coupled to the handpiece housing, the electrode assembly including at least one RF electrode with a dielectric portion configured to contact the tissue and a conductive portion disposed on the dielectric portion, the conductive portion further comprising a portion of a flex circuit, the RF electrode adapted to deliver RF energy to the tissue, and the dielectric portion and the conductive portion being arranged such that the RF energy is capacitively coupled from the conductive portion for delivery into the tissue by transmission through the dielectric portion.

2. The handpiece of claim 1, further comprising:
    a shroud coupled to the handpiece.

3. The handpiece of claim 1, wherein the RF electrode is spring loaded.

4. The handpiece of claim 3, wherein the spring is pre-loaded.

5. The handpiece of claim 3, wherein the spring is configured to bias the RF electrode in a direction toward the handpiece housing.

6. The handpiece of claim 1, wherein the electrode assembly includes a vent.

7. The handpiece of claim 1, wherein the dielectric portion is positioned around at least a portion of a periphery of the conductive portion.

8. The handpiece of claim 1, wherein the dielectric portion is positioned around an entirety of a periphery of the conductive portion.

9. The handpiece of claim 1, further comprising:
    leads coupled to the RF electrode.

10. The handpiece of claim 1, wherein the conductive portion includes metal.

11. The handpiece of claim 1, wherein the electrode assembly is moveable within at least a portion of the handpiece housing.

12. The handpiece of claim 1, wherein the conductive portion includes copper.

13. The handpiece of claim 1, wherein the electrode assembly is slideably moveable within at least a portion of the handpiece housing.

14. The handpiece of claim 1, wherein the dielectric portion includes polyimide.

15. The handpiece of claim 1, wherein the RF electrode includes a copper polyimide composite material.

16. The handpiece of claim 1, wherein the RF electrode is rotatably positioned in the electrode assembly.

17. The handpiece of claim 1, wherein the flex circuit is configured to isolate flow of a cooling fluidic medium from a back surface of the RF electrode to a front surface of the RF electrode.

18. The handpiece of claim 1, wherein the flex circuit is configured to create a reservoir for a cooling fluidic medium that gathers at a back surface of the RF electrode.

19. The handpiece of claim 1, wherein the electrode assembly is coupled detachably to the handpiece housing.

20. The handpiece of claim 1, wherein the electrode assembly is coupled to the handpiece housing in a stationary position.

21. The handpiece of claim 1, wherein the flex circuit includes trace components.

22. The handpiece of claim 1, wherein the flex circuit include a force sensor coupled to the flex circuit.

23. The handpiece of claim 1, wherein the flex circuit includes a thermal sensor.

24. The handpiece of claim 1, wherein the flex circuit further comprises the dielectric portion.

25. The handpiece of claim 1, further comprising:
a force sensor coupled to the RF electrode.

26. The handpiece of claim 25, wherein the force sensor is configured to detect an amount of force applied by the RF electrode against a surface.

27. The handpiece of claim 25, wherein the force sensor is configured to zero out gravity effects of the weight of the electrode assembly.

28. The handpiece of claim 25, wherein the force sensor is configured to zero out gravity effects of the weight of the electrode assembly in any orientation of a front surface of the RF electrode relative to a direction of gravity.

29. The handpiece of claim 25, wherein the force sensor is configured to provide an indication of RF electrode contact with a skin surface.

30. The handpiece of claim 25, wherein the force sensor is configured to provide a signal indicating that a force applied by the RF electrode to a contacted skin surface is below a minimum threshold.

31. The handpiece of claim 25, wherein the force sensor is configured to provide a signal indicating that a force applied by the RF electrode to a contacted skin surface is above a maximum threshold.

32. The handpiece of claim 25, further comprising:
a tare button coupled to the force sensor.

33. The handpiece of claim 1, wherein the handpiece assembly further includes a valve member adapted to control delivery of a cooling fluidic medium that cools the electrode assembly.

34. The handpiece of claim 33, wherein the electrode assembly includes a channel coupled with the valve member for delivery of the cooling fluidic medium, the channel having an inlet and an outlet.

35. The handpiece of claim 34, wherein the outlet of the channel has a smaller cross-sectional area than a cross-sectional area of the inlet.

36. The handpiece of claim 33, further comprising:
a fluid delivery member coupled to the valve member, wherein the fluid delivery member is configured to provide an atomizing delivery of the cooling fluidic medium to the RF electrode.

37. The handpiece of claim 36, wherein the fluid delivery member is positioned in the handpiece housing.

38. The handpiece of claim 36, wherein the fluid delivery member is positioned in the electrode assembly.

39. The handpiece of claim 36, wherein the fluid delivery member includes a nozzle.

40. The handpiece of claim 36, wherein the fluid delivery member is configured to deliver a controllable amount of the cooling fluidic medium to the RF electrode.

41. The handpiece of claim 36, wherein the fluid delivery member is configured to controllably deliver the cooling fluidic medium to a back surface of the RF electrode.

42. The handpiece of claim 36, wherein the fluid delivery member is configured to controllably deliver the cooling fluidic medium to a back surface of the RF electrode to evaporatively cool the RF electrode and conductively cool a skin surface in contact with the front surface of the RF electrode.

43. The handpiece of claim 36, wherein the fluid delivery member is configured to controllably deliver the cooling fluidic medium to a back surface of the RF electrode at substantially any orientation of the front surface of the RF electrode relative to a direction of gravity.

44. The handpiece of claim 33, wherein the electrode assembly is sufficiently sealed to minimize flow of the cooling fluidic medium from a back surface of the RF electrode to a skin surface in contact with a front surface of the RF electrode.

45. The handpiece of claim 33, wherein the valve member is configured to provide a pulsed delivery of the cooling fluidic medium.

46. The handpiece of claim 33, wherein the valve member includes a solenoid valve.

47. The handpiece of claim 1, wherein the electrode assembly is rotatably moveable relative to the handpiece housing.

48. A handpiece for non-invasively treating tissue using RF energy, comprising:
a handpiece assembly including a handpiece housing; and
an electrode assembly coupled to the handpiece housing, the electrode assembly including a thin and flexible flex circuit, the flex circuit including a dielectric layer and a conductive RF electrode layer disposed on the dielectric layer, and at least a portion of the RF electrode layer being capacitively coupled to the tissue when at least a portion of the flex circuit is in contact with a skin surface.

49. The handpiece of claim 48, wherein the flex circuit is configured to isolate flow of a cooling fluidic medium from a back surface of the RF electrode to a front surface of the RF electrode.

50. The handpiece of claim 48, wherein the flex circuit is configured to create a reservoir for a cooling fluidic medium that gathers at a back surface of the RF electrode.

51. The handpiece of claim 48, wherein the flex circuit includes trace components.

52. The handpiece of claim 48, wherein the flex circuit include a force sensor coupled to the flex circuit.

53. The handpiece of claim 48, wherein the flex circuit includes a thermal sensor.

54. The handpiece of claim 48, wherein the flex circuit includes a dielectric portion that contacts the skin surface.

55. The handpiece of claim 48, wherein the handpiece assembly further includes a valve member adapted to control delivery of a cooling fluidic medium that cools the electrode assembly.

56. The handpiece of claim 48, wherein the electrode assembly is coupled detachably to the handpiece housing.

* * * * *

UNITED STATES PATENT AND TRADEMARK OFFICE
CERTIFICATE OF CORRECTION

PATENT NO. : 7,141,049 B2 Page 1 of 2
APPLICATION NO. : 10/072610
DATED : November 28, 2006
INVENTOR(S) : Stern et al.

It is certified that error appears in the above-identified patent and that said Letters Patent is hereby corrected as shown below:

Title Page, Item (56) References Cited: U.S. Patent Documents
Page 1, after "Morrison" delete "", Jr.'"".
Page 4, line 1, change "Pearoe" to --Pierce--.

Column 1:
Line 15, after "particularly" delete ",".
Line 35, remove the hard return after "The".
Line 35, change "Collagen" to --collagen--.

Column 2:
Line 44, after "follicles" insert --,--.
Line 56, after "redness" insert --,--.
Line 57, change "delivery" to --delivering--.

Column 3, line 23, change "design" to --designed--.

Column 4:
Line 37, change "a" to --at--.
Line 41, before "assembly", delete ", a handpiece".
Line 45, change "a" to --at--.

Column 5:
Line 5, after "electrode" delete "that".
Line 5, change "dielectric" to --dialectric--.
Line 25, change "a" to --at--.

Column 7
Line 12, after "be" insert --a--.
Line 20, after "including" insert --,--.
Line 47, after "%" insert --,--.

Column 8:
Line 32, change "Rf" to --RF--.
Line 37, after "of" delete "the".
Line 49, after "be" delete --positioned--.
Line 51, change "preferable" to --preferably--.

UNITED STATES PATENT AND TRADEMARK OFFICE
CERTIFICATE OF CORRECTION

PATENT NO. : 7,141,049 B2
APPLICATION NO. : 10/072610
DATED : November 28, 2006
INVENTOR(S) : Stern et al.

It is certified that error appears in the above-identified patent and that said Letters Patent is hereby corrected as shown below:

Column 9:
Line 4, change "affected" to --effected--.
Line 23, after "is" delete ",".
Line 26, change "Rf" to --RF--.
Line 41, change "moveable" to --moveably--.

Column 10
Line 6, after "as" insert --,--.
Line 13, after "42" insert --,--.
Line 21, after "to" delete ",".
Line 48, after "to" delete ",".

Column 11:
Line 4, after "tissue" insert --.--.
Line 15, change "verse" to --versa--.
Line 53, change "lies" to --lie--.
Line 54, before "two" insert --and--.

Column 14, line 48, claim 52, change "include" to --includes--.

Signed and Sealed this

Fifteenth Day of May, 2007

JON W. DUDAS
*Director of the United States Patent and Trademark Office*